United States Patent
Rehm et al.

(10) Patent No.: US 7,001,737 B2
(45) Date of Patent: Feb. 21, 2006

(54) URINARY TRYPSIN INHIBITOR ASSAY CONTAINING A CHELATING AGENT

(75) Inventors: Gary E. Rehm, Elkhart, IN (US); Michael J. Pugia, Granger, IN (US); Paul F. Corey, Elkhart, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/844,815

(22) Filed: Apr. 30, 2001

(65) Prior Publication Data

US 2001/0055816 A1 Dec. 27, 2001

Related U.S. Application Data

(60) Provisional application No. 60/204,032, filed on May 15, 2000.

(51) Int. Cl.
*G01N 33/573* (2006.01)
*G01N 33/53* (2006.01)

(52) U.S. Cl. ............... 435/7.4; 435/7.71; 435/7.92; 435/23; 435/69.2; 436/518; 422/56; 422/57

(58) Field of Classification Search ............ 435/7.4, 435/7.71, 7.72, 23, 69.2, 174, 176, 183, 184, 435/68.1, 970, 7.92, 288.1; 436/514, 518; 422/56–58, 61
See application file for complete search history.

(56) References Cited

U.S. PATENT DOCUMENTS

| 5,384,247 A | * | 1/1995 | Berry et al. ............... 435/22 |
| 5,595,731 A | * | 1/1997 | Vallieres ................. 424/76.4 |
| 5,618,684 A | * | 4/1997 | Nonobe et al. ............ 435/16 |
| 5,856,117 A | * | 1/1999 | Uenoyama et al. ......... 435/23 |
| 6,130,055 A | * | 10/2000 | Nanbu et al. ............. 435/18 |
| 6,177,268 B1 | * | 1/2001 | Yonehara ................ 435/188 |
| 6,583,108 B1 | | 6/2003 | Tamburini et al. |

FOREIGN PATENT DOCUMENTS

| EP | 0814167 A1 | | 12/1997 |
| GB | 2204398 A | * | 11/1988 |
| WO | WO99/49076 | * | 2/1999 |

OTHER PUBLICATIONS

Ausubel F M: "Current Protocols in Molecular Biology, Passage Text" Current Protocols in Molecular Biology, New York, Wiley & Sons, US, vol. 3, 1995, p. A03F12 XP002054528.

* cited by examiner

*Primary Examiner*—Long V. Le
*Assistant Examiner*—Gary W. Counts
(74) *Attorney, Agent, or Firm*—McDermott Will & Emery LLP

(57) ABSTRACT

Disclosed is an assay for determining the presence and concentration of trypsin inhibitor in urine samples. The assay reagents, which may be used either in the liquid or dry states, include trypsin, a trypsin substrate and a polycarboxylic chelating agent. The inclusion of the chelating agent in the assay has been found to reduce variation in the assay results.

11 Claims, No Drawings

URINARY TRYPSIN INHIBITOR ASSAY CONTAINING A CHELATING AGENT

CLAIM OF PRIORITY

This patent claims priority under 35 U.S.C. § 119(e) to U.S. provisional patent application Ser. No. 60/204,032, filed May 15, 2000.

BACKGROUND OF THE INVENTION

It has long been known that urinary trypsin inhibitor (UTI) is present in human urine, and that its concentration in urine increases due to kidney diseases.

Piette et al report in *The European Journal of Medicine* Vol. 1, 5 Sep. 1992, that urinary trypsin inhibitory activity can be a useful marker, particularly in patients with fever of unknown origin and/or elevated erythrocyte sedimentation rate. Kuwajima et al report in *Clinical Biochemistry*, Vol. 23, April 1990, Pp. 167–171 that the automated assay of urinary trypsin inhibitor may be useful for the clinical diagnosis of acute phase response.

Accordingly, urinalysis for UTI is an important diagnostic tool. Such analytical techniques typically involve contacting the urine sample with a trypsin substrate attached to a chromophore at either arginine or lysine since these are the amino acids which are cleaved by trypsin. The concentration of urinary trypsin inhibitors in the urine sample is inversely proportional to the intensity of the colored response of the chromophore since urinary trypsin inhibitors inhibit trypsin activity according to their concentration in the fluid test sample. In Japanese Public Patent Disclosure Bulletin No. 10-70997, published on Mar. 17, 1998, there is described a method for measuring the degree of inhibition of trypsin activity in urine by mixing a urine sample, an enzyme sample containing trypsin and a buffer together with calcium in the amount of 0.15 $\mu$mol or more per $\mu$g of trypsin in the reaction fluid to a maximum of 100 $\mu$mol calcium per mL of urine sample. In addition, surfactants are used to assist in dissolving the trypsin substrate in its organic solvent. This technique is apparently designed to mask the interference caused by calcium present in urine samples by adding a large excess of calcium to the assay reagents.

This assay technique involves a liquid phase test for trypsin inhibitors in urine using excess calcium to cover up calcium interference and surfactants to dissolve the trypsin substrate. This technique is not suitable for a dry phase assay because the amount of buffer needed in such an assay to overcome the buffer in urine would precipitate in urine.

SUMMARY OF THE INVENTION

The present invention is an assay for trypsin inhibitors in urine which involves contacting a urine test sample with a buffered assay medium comprising trypsin, a substrate for trypsin which will produce a detectable response when cleaved by trypsin and a polycarboxylic chelating agent in sufficient quantity to inhibit interference with the assay from calcium present in the urine test sample, and correlating the concentration of the trypsin inhibitor with the detectable response from the cleaving of the substrate.

Also included within the scope of the present invention is a dry assay device having trypsin, buffer, a trypsin substrate and a chelating agent in an absorbant carrier for detecting the presence and concentration of trypsin inhibitor in urine test samples.

DESCRIPTION OF THE INVENTION

Urinary trypsin inhibitor is a glycoprotein which inhibits the enzyme reactivity of trypsin, α-chymotrypsin, hyaluronidase and creatine phosphokinase. Trypsin inhibitor activity has previously been suggested as a possible screening test for the diagnosis of bacterial infection. When bacterial infections occur, white blood cells are mobilized and the elastase activity of the white blood cells is activated. During the acute phase response, interleukin-1 induces the production of inter-α-trypsin inhibitor which is decomposed by the elastase activity into low molecular weight trypsin inhibitors. These trypsin inhibitors appear to act on the inflamed sites, showing anti-inflammatory and anti-shock activities, prior to being excreted in the urine. Quantitative changes in trypsin inhibitor have been shown to be useful as an index of infection or inflammation. Trypsin inhibitor has also been shown to be elevated under other circumstances such as malignant tumors, kidney disease, myocardial infarction and post surgery. It can be present in minute quantities in the urine of healthy individuals.

Serum C-reactive protein, sialic acid and erythrocyte sedimentation rate have been utilized as markers of infection and inflammation. However, all of these markers are serum based which necessitates a blood draw and time for coagulation, centrifugation and separation of the blood sample prior to analysis. The urinary trypsin inhibitor assay offers an easy, quick and inexpensive means of assessing infection without the necessity of a blood sample. Urine samples can be collected easily and require no pretreatment prior to analysis. Used as a prediagnostic test, trypsin inhibitor assays have an especially high level of utility in the pediatric field where urine samples are particularly easier to obtain than blood samples. Furthermore, it has been demonstrated that trypsin inhibitor correlates well to changes in C-reactive protein and erythrocyte sedimentation rate.

The assay of the present invention is based on the discovery that the interference with the urine trypsin assay caused by the presence of calcium ion in urine can be factored out of the assay by the use of certain chelating agents. This was unexpected because the chelating agents were not used to extract and remove calcium but only to complex the salt. It was to be expected that trypsin would still interact with the complexed salt in a detrimental fashion.

The assay can be carried out in the liquid phase by dissolving the assay reagents in an aqueous or polar aprotic solvent; for example; water, ethanol, methanol, isopropanol, acetonitrile, dimethylsulfoxide, acetone, dimethylformamide or methyl ethyl ketone. At a minimum, the solution will contain trypsin at a concentration of from 10 to 750 IU/mL (preferably 100 to 500 IU/mL), a trypsin substrate typically in a concentration of from 0.2 to 5.0 mM with a concentration of 0.5 to 2.0 mM being preferred, a chelating agent at a concentration of from 0.2 to 50 mM (preferably 10 to 25 mM) and a buffer such as phosphate to maintain the solution's pH at a level of from 6.0 to 9.0 with a pH of 7.0 to 8.0 being preferred.

One aspect of the present invention is directed to an analytical test strip for the detection of trypsin inhibitor in the urine sample. The strip comprises an absorbant carrier through which the urine test sample can flow which is impregnated with the reagent system. The absorbant carrier used for the test strip is preferably a filter paper. Other materials useful as the absorbant carrier include felt, porous ceramic strips and woven or matted glass fibers. Also suitable are wood, cloth and sponge material.

In preparation, the strip is typically impregnated with an aqueous solution of buffer, chelating agent, trypsin, and optionally a surfactant followed by drying. The strip is then impregnated with a solvent solution of the trypsin substrate and dried.

Preferred chelating agents are those aminocarboxylic acids possessing at least one complex forming groups of the formula —N(CH$_2$CO$_2$H)$_2$ including iminodiacetic acid; nitrilotriacetic acid; diethylenetriamine pentaacetic acid; triethylenetriamino hexa-acetic acid; 2,3-propylenediamine tetra-acetic acid and 1,2-diaminocyclohexane tetra-acetic acid.

Suitable trypsin substrates for use in the present invention are those compounds which contain lysine or arginine linkages which are cleavable by trypsin to form a colored species which can be detected either visually or by spectrophotometric means. Such substrates include benzyol-L-arginine p-nitro anilide. Other trypsin substrates which are suitable for use in the present invention include but are not limited to arginine or lysine amide derivatives of 7-amino-4-methylcoumarin, 2-aminonaphthalene, 4-methoxy-2-aminonaphthalene, 3-carboxy-4-hydroxy-analine, 2-chloro-4-nitro-analine, 3-aminoindole, 2-aminoacridone, 2-aminobenzothiazole, 2-aminopyrimidine, Rhodamine 110 and 6-aminoguinoline. Various esters and amides have also been used as substrates for the detection of proteases such as trypsin. A new class of substrates which includes Nα,N$_G$-blocked-nitro-L-arginine esters of aromatic alcohols such as 3-(Nα-Tosyl-N$_G$-nitro arginyloxy)-5-phenylpyrrole as disclosed in co-pending application Ser. No. (identified as MSE #2609 and filed on even date with this application) are also suitable. This trypsin substrate is particularly suitable in the dry reagent format because of its nitro protecting group which prevents reaction between the trypsin and substrate before the strip is wetted with the urine test sample.

The method of practicing the present invention is further illustrated by the following examples:

EXAMPLE I

Initial testing of a modified liquid assay for urinary trypsin inhibitors was carried out using the following assay system:

The assay procedure was carried out on a Cobas Fara spectrophotometer (Roche Diagnostics). A 10 μL aliquot of urine as test sample was added to 120 μL of an aqueous buffer solution comprised of a 50 mM sodium dihydrogen phosphate either with or without 0.47 g/L of EGTA. The maximum practical amount of calcium in urine was determined to be 80 mg/dL based on published data and double the amount of EGTA (0.47 g/L) needed to complex this amount of calcium was added to the assay system. Secondly, 100 μL of a 32 mg/L trypsin enzyme aqueous solution was added and the combined solutions were mixed for 2 minutes at 25° C. Finally, 100 mL of a substrate solution comprised of 0.70 g/L of benzyol-L-arginine p-nitro anilide (BAPNA) in DMSO was added. The resultant mixture was centrifuged and read at 15 second intervals for 8 minutes at 405 nm.

Three urine samples void of inhibitor were each used to prepare 5 specimens with 50, 150, 250 and 350 of urine trypsin inhibitor (UTI) activity per liter (IU/L) by adding urinastatin (a glycoprotein with a molecular weight of 67,000 g/mol and an isoelectric point of 2.4 sold under the trade name Miraclid). The urine samples were tested using this assay system in which changes in substrate color were detected on the Roche Cobas-Fara Clinical Analyzer. This validation study was carried out for the purpose of demonstrating reduced variation in the assay when EGTA was included. The results are set out in the following Tables A and B.

TABLE A

Results for Liquid Assay System Without EGTA Observed for 3 Replicates

|  |  | 0 | 50 | 150 | 250 | 350 |
|---|---|---|---|---|---|---|
| Urine 1 | Rep 1 | −3.72 | 30.12 | 134.69 | 234.68 | 307.45 |
|  | Rep 2 | −5.89 | 22.71 | 136.6 | 229.7 | 305.19 |
|  | Rep 3 | −15.5 | 26.343 | 142.49 | 223.8 | 305.49 |
| Urine 2 | Rep 1 | −81.51 | −13.44 | 87.25 | 217.14 | 302.65 |
|  | Rep 2 | −79.73 | −17.76 | 104.21 | 211.66 | 301.33 |
|  | Rep 3 | −66.52 | 1.97 | 102.44 | 224.7 | 302.48 |
| Urine 3 | Rep 1 | −37.16 | 19.98 | 114.31 | 206.3 | 294.27 |
|  | Rep 2 | −36.31 | 19.61 | 117.17 | 212.5 | 293.53 |
|  | Rep 3 | −26.43 | 7.5 | 110.01 | 224.77 | 293.42 |

Urine 1 = SG of 1.006 and calcium chloride - 25 mg/dL
Urine 2 = SG of 1.018 and calcium chloride - 11 mg/dL
Urine 3 = SG of 1.032 and calcium chloride - 16 mg/dL

TABLE B

Results for Liquid Assay System With EGTA Observed for 3 Replicates

|  |  | 0 | 50 | 150 | 250 | 350 |
|---|---|---|---|---|---|---|
| Urine 1 | Rep 1 | 11.159 | 49.07 | 147.403 | 250.993 | 303.859 |
|  | Rep 2 | 14.453 | 52.505 | 152.336 | 251.909 | 302.132 |
|  | Rep 3 | 5.188 | 51.244 | 147.269 | 253.333 | 301.423 |
| Urine 2 | Rep 1 | 11.711 | 64.09 | 154.956 | 246.452 | 300.167 |
|  | Rep 2 | 13.969 | 64.112 | 153.48 | 242.246 | 300.547 |
|  | Rep 3 | 28.846 | 69.656 | 150.433 | 240.892 | 300.405 |
| Urine 3 | Rep 1 | 36.406 | 76.775 | 162.92 | 258.598 | 305.314 |
|  | Rep 2 | 31.243 | 76.924 | 170.404 | 261.391 | 303.783 |
|  | Rep 3 | 32.565 | 80.051 | 168.073 | 254.707 | 303.637 |

From Tables A and B, it can be determined that there was great variability in results between the various urine samples when EGTA was not in the assay solution. The standard error for Table A is 19.02 IU/L whereas the standard error for Table B (EGTA included) is 10.53 IU/L. Thus, EGTA reduces variation between urine samples having increasing amounts of calcium. The three urine test samples had varying amounts of calcium; the higher the calcium level, the further the observed result was from the expected result. This agreed with other standard solutions that showed calcium to be inhibitor of trypsin. Analysis of other urinary components such as other salts, specific gravity and pH did not demonstrate correlation between the expected and observed results. The testing of a number of combinations of potential urine trypsin activators and inhibitors was carried out with the result that calcium was determined to increase their activity while chloride, sodium and magnesium were found to have little effect. It was further determined that the calcium either had to be overwhelmed or complexed to remove it from the assay system. Since the long term goal is to produce a dry phase test for urinary trypsin inhibitors, and the calcium would precipitate most buffers, it was decided to try to remove the calcium by complexing.

Buffers are needed since the trypsin enzyme is pH dependent and a constant pH of from about 7.0 to 8.0 is desirable to obtain a fixed activity. Phosphate and carboxyl groups are common as the charged ionizable groups of buffering agents and calcium salts of these groups are not very water soluble (calcium phosphate is relatively insoluble), so they tend to precipitate from solution.

EXAMPLE II

A modified liquid phase assay was used in this experiment. The liquid assay used:

i. 0.1 mL of 10% surfactant (as shown in Table C)
ii. 3 mL buffer
iii. 0.5 mL H$_2$O (with and without added NaCl)
iv. 0.9 mL of MMBD diazonium (125 mg/25 mL)
v. 0.2 mL of enzyme (10 mg trypsin/100 mL)
vi. 0.3 mL substrate 3-(Nα-tosyl-N$_G$-nitro-L-arginyloxy)-5-phenylpyrrole (20 mg/50 mL acetone)

Analyses for trypsin inhibitor in 3 urine specimens were carried out as in the previous examples with the absorbance results being set out in Table C. The 3 urine specimens tested were:

Specimen 1=normal urine lacking trypsin inhibitor,
Specimen 2=same normal urine containing 250 IU/L trypsin inhibitor, and
Specimen 3=same normal urine containing 250 IU/L trypsin inhibitor plus urea, calcium, magnesium, sodium and potassium at 10 fold the physiological limit.

TABLE C

UTI Liquid Assay Results With Surfactants

| Surfactant | Negative* Specimen 1 | Positive Specimen 2 | Positive Specimen 3 with salts | Class |
|---|---|---|---|---|
| None | 117 | 541 | 438 | 1 |
| Aerosol OT (Gelled) | 40 | 253 | 324 Cloudy | 2 |
| Tween-80 | 1 | 201 | 102 | 3 |
| Triton X-100 | 15 | 177 | 81 | 3 |
| Surfynol | 107 | 627 | 469 | 1 |
| Ninate 411 | 13 | 19 | 78 | 4 |
| Benzalkonium Cl | 143 | 269 | 7 | 5 |
| Standopol ESL | 23 | 214 | 245 | 2 |
| Bio-Terge AS-40 | 22 | 81 | 211 | 2 |
| Sodium Cholate | 128 | 492 | 421 | 1 |
| Zonyl 100 | 48 | 408 | 225 | 3 |
| Tetronic 1307 | 109 | 652 | 336 | 3 |
| SDS | 15 | 6 | 20 | 4 |
| Span 60 | 115 | 199 | 439 Precipitate | 2 |
| Igepal CA-210 | −271 | 281 | 114 V Cloudy | 3 |
| Pluronic L64 | 71 | 501 | 294 | 3 |
| Chremophor EL | 11 | 166 | 77 | 3 |
| Silwet L7600 | 32 | 358 | 188 | 3 |
| Surfactant 10G | 45 | 451 | 258 | 3 |
| Brij 35 | 13 | 206 | 88 | 3 |
| Rhodasurf ON-870 | 1 | 141 | 56 | 3 |
| Geropon T-77 | 5 | 22 | 32 | 4 |

Calculation of absorbance result is 1000* ((Peak @ 2 min - 700 nm @ 2 min) - (Peak @ 0 min - 700 nm @ 0 min))
*(No surfactant)

From Table C it can be determined that good reactivity and mixture level discrimination were possible with aqueous solutions of trypsin inhibitor but that the presence of any surfactant in the assay causes significant variations. Not only is the negative specimen affected, but the differences between the two positive specimens is magnified and is dependent on the nature of the surfactant.

EXAMPLE III

Twenty-two different surfactants were tested as described in Example II and Table C. This testing showed that the following 5 classes of surfactant existed:

i. Those which had no effect on blank or reactivity;
ii. Those which increased both blank and reactivity;
iii. Those which decreased both blank and reactivity;
iv. Those which increased reactivity with added salt; and
v. Those which decrease reactivity with added salt.

Strips were made with one surfactant from each class by preparing first and second solutions according to the following procedure: Filter paper (204 C grade from Alstrom Inc.) was saturated with the first dip solution and dried for 15 minutes at 90° C. The resultant reagent was saturated with the second dip solution and dried for 10 minutes at 90° C. to form the completed reagent strip. Adhesive (Y9494 from 3M Inc.) was applied to the reagent strip and it was affixed to a polystyrene handle in the form of pads which were 0.86 cm×0.86 cm square.

A. Components for first dip.
a. 50 mL water
b. Phosphate Monobasic Buffer (5.00 g)
c. Surfactant (Ninate 411, Aerosol OT, Tween 80, BioTergr AS-40 or none)
d. 5.1 mM (0.119 g) Ethylene glycol bis (β-aminoethyl ether) N,N,N',N'-tetraacetic acid (EGTA)
e. 1.75% Plasdone (0.877 g) (PVP K30 from Sigma-Aldrich)
f. 340 U/mL Trypsin Enzyme
g. 1.75 mM MgSO$_4$ (2.16 g)
h. 2.70 mM (43.7 mg) 2-Methoxy-4-morpholino-benzene diazonium chloride, zinc chloride (MMBD) (diazonium coupling agent)
i. Adjust to pH 7.80±0.02 with 1N NaOH.

B. Components for second dip.
a. 19.3 mg or 0.75 mM 3-(Nα-tosyl-N$_G$-nitro-L-arginyloxy)-5-phenylpyrrole
b. 50 mL of Acetone The data were collected by dipping the strips into the urine formulations set out in Table D and then placing them in a CLINITEK™ 50 spectrometer from Bayer Diagnostics to collect data at 15 and 60 seconds after dipping and to calculate a decode figure by using the equation decode={[(B15+G15)−(B60+G60)]/(B15+G15)}* 1000.
Where:

B15 is the reflectance of the blue wavelength at 15 seconds,
B60 is the reflectance of the blue wavelength at 60 seconds,
G15 is the reflectance of the green wavelength at 15 seconds, and
G60 is the reflectance of the green wavelength at 60 seconds.

The decode value is directly proportional to the UTI concentration. A result of >180 is assigned 0 IU/mL whereas a result of <120 is assigned a value of 250 IU/mL.

The results of this experiment are presented in Table D.

TABLE D

Lack of Surfactant in Strip Assay for UTI

| | Decode Result | | |
|---|---|---|---|
| Surfactant | Negative Specimen 1 | Positive Specimen 2 | Positive Specimen 3 |
| None | 193 | 107 | 95 |
| Ninate 411 | 179 | 92 | 87 |
| Aerosol OT | 182 | 109 | 82 |
| Tween 80 | 185 | 97 | 81 |
| Bioterge AS-40 | 197 | 85 | 94 |

Specimen 1 = urine
Specimen 2 = urine with 250 IU/L of trypsin inhibitor
Specimen 3 = urine with 250 IU/L of trypsin inhibitor with salts Table D shows that the presence or absence of surfactant in the dry reagent has no effect or benefit for reducing interference since a large response to trypsin inhibitor was found without surfactant.

The results, as presented in Table D, were not as expected since a strong surfactant effect was noted in the absence of EGTA as reported in Table C. The urine pH was adjusted to 7.5–8.0, the optimum strip pH to remove any effect of buffering. All assays which included a surfactant showed no improvement over water. This study led to the conclusion that the formula with EGTA is less prone to the effects of surfactant than that without. Due to the assay variability caused by surfactants, they may be omitted from the assay formulation. However, in those formulations in which difficulty is encountered in getting the substrate into solution, a non-ionic polyoxyalkyl surfactant for example, one containing ethyleneglycol units may be used. This class of surfactant includes Aerosol OT, Ninate 411 and Bioterge A-40. These surfactants were found not to have an adverse effect on the reproducibility of the assay.

EXAMPLE IV

Further strip development used no surfactant and concentrated on improving the buffer capacity of the strip. A series of strip formulations was made with increasing levels of buffer. It was determined that enough phosphate buffer (>1 M) to overcome the urine pH effect could not be dissolved in the dip solution. Only a few organic buffers can be dissolved in water to such an extent that they overcome the urine buffering capacity; Tris [Tris(hydroxymethyl) amino methane] is one of them. In this example Tris was used at a level of 1.5 M to provide a pH of 7.8. The formulation and procedure for preparing the strips was the same as that used in Example III except that the buffer was 1.3 M tris (7.87 g in 50 mL of water) and there was no surfactant added to the formulation.

The purpose of the study described in this Example IV was to demonstrate the correlation of a strip assay to the immunological liquid assay reference method which is described by T. Noad in Osaka-stii Igakkai Zasshi Vol. 44, No. 2 June 1992; 485–500. The 911 clinical urines were assessed using the immunological reference method developed as shown in Example II using a Hitachi 7070 Autoanalyzer and an antibody kit from Eiken Japan. Analytical parameters are as follows:

1) Method: 2 point end
2) Measuring Times: $1^{st}$ time, 355.35 sec; $2^{nd}$ time, 590.94 sec;
3) Wavelength: 660 nm
4) Sample Dilution: 100 times with pH 7.4 buffer (standard)/50 times with pH 7.4 buffer (in low concentration specimen)
5) Sample Value: 5 µL
6) Reagent Value: $1^{st}$ reagent 150 µL; $2^{nd}$ reagent 50 µL
7) Standard Point: 7 points (0, 7.8, 15.6, 31.3, 62.5, 125, 250 IU/mL)
8) Standard Curve: Spline.

Table E is a truth table showing the correlation of the strip assay of this Example and the immunological liquid assay reference. Overall, the correlation between the two methods is good as shown by comparing the agreement at the 0, 100 and 200 strip results with immunoassay results at <50, 50–150 and >150 IU/mL in Table E. The decode ranges and equations used to obtain the values for 0, 100 and 200 where a decode of ≧275 is a "0", 200–275 is a "100" and a decode of <200 is a strip result of "200". Positive and negative agreements were 66.7 and 88.5% for the immunological method at a threshold of 50 IU/mL and within the reasonable range for a strip test. Normal individuals were found to have <50 IU/mL in the 99% of the cases.

TABLE E

Truth Table for TI Immunoassay Reference vs. TI Strip Result

| Strip TI Result (U/mL) | Immunoassay TI Result (U/mL) | | | Total |
|---|---|---|---|---|
| | <50 | 50–150 | >150 | |
| 0 | 639 (89.5%) | 66 (36.4%) | | 705 |
| 100 | 74 (10.4%) | 108 (39.7%) | 2 (11.8%) | 184 |
| 200 | 1 (0.1%) | 7 (3.9%) | 15 (88.2%) | 23 |
| Total | 714 (78.2%) | 181 (19.9%) | 17 (1.9%) | 912 |

Of the clinical urine samples, 898 were additionally assessed using a creatinine strip as described in U.S. Pat. No. 5,733,787 and the quantative Jaffe creatine assay on the Cobas-Fara analyzer. A truth table showing the correlation of the ratio of the strip assay of Example IV ratioed to the creatinine strip compared to the immunological liquid trypsin inhibitor assay ratioed to the creatinine reference method is shown in Table G. The creatinine reference method was the commercially available assay for the COBAS-FARA instrument from Roche Diagnostics. Overall, the correlation between the two methods was good as determined by comparing strip results with immunoassay results at three levels, i.e. <50 IU/g, 50–150 IU/g and >150 IU/g representing clinically normal, abnormal and high abnormal specimens. A decode ratio result is obtained by dividing the TI reagent decode by the creatine reagent decode. The creatinine decode is the reflectance at the red wavelength/reflectance at the green. The decode ratio result of ≧85 is a strip result of "0", 84.9 to 50 is a strip result of "100" and <50 is a strip result of "200". Agreement of positive and negative results with the immunoassay at a threshold of <50 IU/g were 85.2% and 86.4% which is within the reasonable range for a strip test.

TABLE F

Truth Table for TI/CRE by + Jaffe Methods Immunoassay vs TI/CRE Ratio by Strip

| TI Strip/ CRE Strip (IU/gm) | TI Immunoassay/CRE by Jaffe | | | (IU/gm) |
|---|---|---|---|---|
| | <50 | 50–150 | >150 | |
| 0 | 729 (86.4%) | 8 (16.3%) | | 737 |
| 100 | 111 (13.4%) | 40 (81.6%) | 1 (20%) | 154 |
| 200 | 2 (0.3%) | 1 (2.1%) | 4 (80%) | 7 |
| Total | 844 (94.0%) | 49 (5.5%) | 5 (0.5%) | 898 |

What is claimed is:

1. An assay for trypsin inhibitors in urine which comprises (a) contacting a urine test sample with a buffered assay medium comprising (i) trypsin in an amount of from 10 to 750 IU/mL, (ii) a substrate for trypsin which will produce a detectable response when cleaved by trypsin present in a concentration of from 0.2 to 50 mM and (iii) a polycarboxylic chelating agent present in an amount of from 0.2 to 50 mM, and (b) correlating the concentration of trypsin inhibitor with the detectable response from the cleaving of the substrate, wherein the polycarboxylic chelating agent reduces variation in detected amounts of trypsin inhibitor caused by the presence of calcium ions in the urine in reference to a control sample lacking the polycarboxylic chelating agent.

2. The assay of claim 1 wherein the assay reagents are in solution.

3. The assay of claim 2 wherein the solvent used to form the solution is an aqueous or polar aprotic solvent.

4. The assay of claim 3 wherein the solvent is water, ethanol, methanol, isopropanol, acetonitrile, dimethyl sulfoxide, acetone, dimethylformamide or methylethylketone.

5. The assay of claim 1 wherein the assay reagents are in a dry phase.

6. The assay of claim 5 wherein the assay reagents are impregnated into a dry test device of a material through which the urine test sample can flow by dipping the dry test device into the buffered assay medium with subsequent drying of the solvent.

7. The assay of claim 1 wherein the chelating agent is ethylene glycol bis (β-aminoethyl ether) N,N,N',N'-tetraacetic acid (EGTA); ethylenediaminetrata acetic acid (EDTA); iminodiacetic acid (IDA); nitrilotriacetic acid (NTA); diethylenetriaminipentaacetic acid (DTPA); triethylenetriamine-hexa-acetic acid (TTHA); 2,3-propylenediamino-tetra-acetic acid (UEDTA) and 1,2-diaminocyclohexanetetra-acetic acid.

8. The assay of claim 1 wherein the trypsin concentration is from 100 to 500 IU/mL, the chelating agent is present in a concentration of from 10 to 25 mM, and the pH is at a level of from 7.0 to 8.0.

9. The method of claim 1 wherein the substrate for trypsin is selected from the group consisting of arginine or lysine derivatives of 7-amino-4-methylcourmarin, 2-aminonaphthalene, 4-methoxy-2-amino-naphthalene, 3-carboxy-4-hydroxy-analine, 2-chloro-4-nitro-analine, 3-aminoindole, 2-aminoacridone, 2-aminobenzothiazole, 2-aminopyrimidine, Rhodamine 110 and 6-aminoquinoline.

10. The method of claim 1 wherein the buffer is selected from the group comprising (a) phosphate group containing buffers, (b) carboxyl group containing buffers and (c) Tris buffers.

11. The method of claim 1 wherein the buffer is selected from the group comprising (a) phosphate group containing buffers and (b) carboxyl group containing buffers.

* * * * *